United States Patent [19]

Umezawa et al.

[11] 4,163,839
[45] Aug. 7, 1979

[54] ISOCOFORMYCIN AND A PROCESS FOR THE PRODUCTION THEREOF

[75] Inventors: Hamao Umezawa; Tomio Takeuchi, both of Tokyo; Shinichi Kondo, Yokohama; Masami Shimazaki, Kokunbunji, all of Japan

[73] Assignee: Zaidan Hojin Biselbutsu Kagaku Kenkyu Kai, Tokyo, Japan

[21] Appl. No.: 858,928

[22] Filed: Dec. 9, 1977

[51] Int. Cl.² .................. C07H 19/04; A61K 31/70
[52] U.S. Cl. ................................... 536/24; 424/180
[58] Field of Search .................................... 536/24

[56] References Cited

U.S. PATENT DOCUMENTS

| | | | |
|---|---|---|---|
| 3,616,208 | 10/1971 | Howell | 195/28 N |
| 3,923,785 | 12/1975 | Ryder | 260/211.5 R |
| 3,929,762 | 12/1975 | Umezawa | 536/17 |
| 3,959,257 | 5/1976 | Umezawa | 536/24 |
| 4,014,769 | 3/1977 | Umezawa | 204/158 R |

OTHER PUBLICATIONS

Ohno, et al., J. Am. Chem. Soc., 96, 4326–4327 (1974).
T. J. van Bergen et al., J. Org. Chem., 36, 978 (1971).
Woo, P. W. K. et al., J. Heterocyclic Chem., 11, 641–643 (1974).
Ohno et al., J. Am. Chem. Soc., 96, 4327–4328 (1974).

Primary Examiner—Johnnie R. Brown
Assistant Examiner—Blondel Hazel
Attorney, Agent, or Firm—Herbert W. Taylor, Jr.

[57] ABSTRACT

A novel, unique nucleoside, 3-β-D-ribofuranosyl-3,6,7,8-tetrahydroimidazo[4,5-d][1,3]diazepin-7-ol, named isocoformycin, of the formula

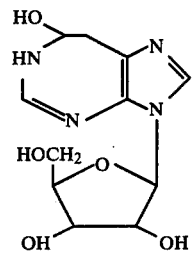

is provided by ring expansion of derivatives of 9-β-D-ribofuranosyl-6-hydroxymethyl-1,6-dihydropurine. Isocoformycin markedly inhibits deaminating enzymes which inactivate formycin and adenine arabinoside (also known as ara-A and Vidarabine). Formycin and adenine arabinoside are used as antiviral and antitumor agents in mammals and birds and isocoformycin is advantageous to prolong the activity and effect of formycin and adenine arabinoside.

1 Claim, No Drawings

ISOCOFORMYCIN AND A PROCESS FOR THE PRODUCTION THEREOF

BACKGROUND OF THE INVENTION

1. Field of the Invention

The present invention relates to a novel organic compound named isocoformycin which is a seven-membered ring nucleoside produced by chemical synthesis and found to inhibit the deaminating enzymes which inactivate formycin and adenine arabinoside. The latter two compounds are used as antiviral and antitumor agents.

2. Description of the Prior Art

M. Ohno et al., J. Am. Chem. Soc., 96, 4326–4327 (1974) is directed to the total syntheses of coformycin starting from a purine ribonucleoside. Coformycin is a unique nucleoside, having a moiety of 3,6,7,8-tetrahydroimidazo[4,5-d][1,3]diazepin-8(R)-ol as the base moiety and has an interesting biological property. See also the article following on pages 4327–4328 and U.S. Pat. Nos. 3,959,257 and 4,014,769.

P. W. K. Woo et al, J. Heterocyclic Chem., 11, 641–643, (1974) is directed to an isolation of a potent adenosine and ara-A deaminase inhibitor in crystalline form from the fermentation broth of a strain of Streptomyces antibioticus and to the structural elucidation of said compound. See also U.S. Pat. No. 3,616,208.

T. J. van Bergen et al., J. Org. Chem., 36(7), 978–983, (1971) is directed to the ring expansion of the tosylate of 3,5-dicarbomethoxy-2,6-dimethyl-2-hydroxymethyl-1,2-dihydropyridine.

SUMMARY OF THE INVENTION

The present invention relates to a novel organic compound and more particularly relates to a novel seven-membered ring nucleoside and a process for the production thereof.

The novel compound, 3-$\beta$-D-ribofuranosyl-3,6,7,8-tetrahydroimidazo[4,5-d][1,3]-diazepin-7-ol, named isocoformycin, can be represented by the formula:

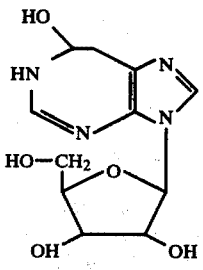

The novel compound of the present invention, isocoformycin, is an analogue of coformycin which is the most potent inhibitor of adenosine deaminase ever known [M. Ohno, N. Yagisawa, S. Shibahara, S. Kondo, K. Maeda and H. Umezawa, J. Am. Chem. Soc., 96, 4326 (1974)]. Recently Woo and Dion reported the isolation of a potent adenosine and ara-A deaminase inhibitor, 2'-deoxycoformycin, from the fermentation broth of a strain of Streptomyces antibioticus [P. W. K. Woo and H. W. Dion, J. Heterocyclic Chem. 11,641 (1974)]. Isocoformycin is the first synthetic nucleoside with a seven-membered ring as a base moiety.

Physical constants of isocoformycin are as follows:

(1) m.p.: 185°–190° C.(dec).
(2) $[\alpha]_D^{25}$: $-58°$ C.(3.0, $H_2O$)
(3) UV: $\lambda_{max}^{MeOH}$ 281 nm(9600)
(4) MS: 284(M+), 266(M—$H_2O$), 252, 193, 163, 149 135, 134, 121
(5) IR(KBr): 3300, 2900, 1720, 1630, 1485, 1440, 1390, 1280, 1200, 1040–1100 $cm^{-1}$
(6) $^1$H-NMR($D_2O$, 100 MHz): $\delta$3.52(2H, m, 8-$CH_2$), 4.27(2H, m, 5'-$CH_2$), 4.6–5.1(3H, 2', 3', 4'-H), 5.84(1H, m, 7-CH), 6.27(1H, d-d, 1'-H), 7.47(1H, s), 8.18(1H, d)
(7) $^{13}$C-NMR($D_2O$, XL-100), Chemical shift (ppm) from an external TMS using dioxane (67.4 ppm) as an internal standard:

| | | | |
|---|---|---|---|
| $C_1'$ 88.5 PPM | | $C_2$ 146 PPM | |
| $C_2'$ 71.5 | | $C_5$ 134 | |
| $C_3'$ 74.1 | | $C_7$ 74.5 | |
| $C_4'$ 86.4 | | $C_8$ 36.6 | |
| $C_5'$ 62.6 | | $C_9$ 125 | |
| | | $C_{10}$ 133 | |

(8) TLC on silica gel:
  Rf=0.12 in EtOAc-MeOH-$H_2O$ (4:1:1)
  Rf=0.31 in n-BuOH-EtOH-$CHCl_3$-17%$NH_4OH$ (4:5:2:2)

The novel compound of the present invention, isocoformycin (III), is useful because of its ability to inhibit strongly the deamination of formycin, adenine arabinoside and cordycepin by the adenosine deaminase present in mammals and birds. The inhibitory activities of isocoformycin on adenosine deaminase were measured using formycin and adenosine as the substrate. Three ml of a solution of adenosine or formycin in 0.05 M phosphate buffer (12 mg/ml, pH 7.5 and 6.5, respectively) was put in a quartz cell of 1 cm in length and 0.1 ml of a solution containing a known amount of isocoformycin in distilled water was added. The reaction was started by addition of 0.1 ml of enzyme solution (adenosine deaminase from calf intestine: 1 mg/ml of 0.025 M ammonium acetate or Takadiastase-Y: 4 mg/ml of distilled water) and the decreases for 2 minutes in optical densities at 265 nm in the case of adenosine or 295 nm in the case of formycin were recorded on Beckmann spectrophotometer equipped with the Gilford recorder. The concentration of the inhibitor for 50% inhibition ($ID_{50}$) was calculated from the difference of the optical densities as shown in Table 1.

Table 1.

| Enzymes Substrates Inhibitors | $ID_{50}$ (mole/liter) | | | |
|---|---|---|---|---|
| | Adenosine deaminase from calf intestine at 25° C. | | Takadiastase-Y at 45° C. | |
| | Adenosine | Formycin | Adenosine | Formycin |
| Isocoformycin | $8.6 \times 10^{-8}$ | $3.5 \times 10^{-8}$ | $1.1 \times 10^{-6}$ | $2.0 \times 10^{-6}$ |

Table 1.-continued

| Enzymes Substrates Inhibitors | ID$_{50}$ (mole/liter) | | | |
|---|---|---|---|---|
| | Adenosine deaminase from calf intestine at 25° C. | | Takadiastase-Y at 45° C. | |
| | Adenosine | Formycin | Adenosine | Formycin |
| 9-β-D-ribofuranosyl-6-hydroxymethyl-1,6-dihydropurine | $5.8 \times 10^{-6}$ | $2.6 \times 10^{-6}$ | $2.8 \times 10^{-4}$ | $2.0 \times 10^{-4}$ |

As indicated in Table 1, the inhibitory activity of isocoformycin against deamination of formycin or adenosine is stronger than that of 9-β-D-ribofuranosyl-6-hydroxymethyl-1,6-dihydropurine known as an inhibitor of adenosine deaminase.

The isocoformycin is also useful as a strong synergist of formcyin and adenine arabinoside for their antitumor activities. Isocoformycin showed a strong synergistic effect with formycin in the inhibition of cell multiplication in tissue cultures. The inhibitory effect of formycin with or without isocoformycin on multiplication of the mouse leukemia L-1210 cells measured by the Lowry method [O. H. Lowry, N. J. Rosenbrough, A. L. Farr and R. J. Randall, J. Biol. Chem., 193, 265 (1951)] is directed in Table 2.

| No. | Formycin | Isocoformycin | Inhibition (%) |
|---|---|---|---|
| 1 | 0.0 μg/ml | 0.0 μg/ml | 0 |
| 2 | 0.20 | 0.0 | 8 |
| 3 | 0.0 | 0.20 | 0 |
| 4 | 0.0 | 0.50 | −4 |
| 5 | 0.20 | 0.20 | 42 |
| 6 | 0.20 | 0.50 | 55 |

Moreover, a marked prolongation in the survival period of mice implanted with the mouse leukemia L-1210 cells has been observed after treatment with formycin combined with isocoformycin intraperitoneally, as shown in Table 3.

Table 3

Prolongation rates in the survival period of mice with L-1210 by treatments of uz,7/26 formycin with or without isocoformycin

| | | Formycin (50 μg/m) | | | |
|---|---|---|---|---|---|
| | | Without | | with | |
| No. | Isocoformycin | s.period | T/C % | s.period | T/C % |
| 1 | 50 μg/m | 8.0 | 93 | 15.0 | 174 |
| 2 | 25 | 10.0 | 93 | 15.0 | 174 |
| 3 | 12.5 | 8.5 | 116 | 14.0 | 163 |
| 4 | 6.2 | 9.0 | 99 | 12.0 | 140 |
| 5 | 3.1 | 9.0 | 105 | 14.0 | 163 |
| 6 | 1.5 | 8.0 deep | 93 | 12.5 | 145 |
| 7 | 0 | 8.6 | 100 | 10.5 | 122 |

Each dose was injected i.p. 2 hrs. after implantation of 10$^5$ L-1210 cells once a day for 10 days.

"S. period" is the mean survival time in days.

"T/C" is the ratio of the mean survival time of the treated (with drug) animals versus the control's (no drug) and is expressed as a percentage.

The novel compound of the invention, isocoformycin, has also an ability to maintain the activity of formycin against Gram-negative bacteria. For example, on a nutrient agar medium containing formycin at the concentration of 50 μg/ml the inhibition diameter against *Escherichia coli* NIHJ was measured by a disc method (8 mm) at the following concentration of isocoformycin.

| Isocoformycin (μg/ml) | Diameter (mm) |
|---|---|
| 200 | 36.0 |
| 40 | 32.0 |
| 10 | 25.0 |
| 2.5 | 22.0 |

Isocoformycin itself has no inhibitory activity without formycin against *Escherichia coli* NIHJ at the concentration of 2 mg/ml.

Isocoformycin of the present invention is prepared in the following ways.

One method (hereinafter referred to as Method-A) consists in treating a sulfonate of 9-β-D-ribofuranosyl-6-hydroxymethyl-1,6-dihydropurine protected on hydroxyl groups in the ribose moiety of the formula:

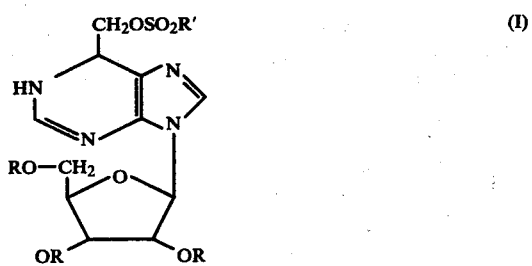

(I)

wherein
R is the same or different and represents a member selected from the group consisting of an acyl residue of an unsubstituted or halosubstituted fatty acid having 2–12 carbon atoms, benzoyl, lower alkyl (C$_1$–C$_4$)-, lower alkoxy (C$_1$–C$_4$)- or halosubstituted benzoyl, isopropylidene, trityl, and lower alkyl (C$_1$–C$_4$)-, halo-, or lower alkoxy (C$_1$–C$_4$)-substituted trityl;

R' represents an unsubstituted or lower alkoxy (C$_1$–C$_4$)-substituted lower alkyl (C$_1$–C$_4$), phenyl, lower alkyl (C$_1$–C$_4$)- or halophenyl, benzyl, and p-nitrobenzyl groups with a base. All ranges given herein, such as 2–12 carbon atoms or "C$_1$–C$_4$" meaning 1–4 carbon atoms, are inclusive.

Another method (hereinafter referred to as Method-B) consists in deblocking the protective groups represented by R in the compound (I) to prepare a compound of the formula:

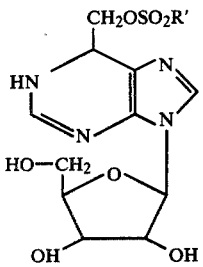

(II)

wherein R' represents the same as in the compound (I); and treating the compound (II) with a base.

Generally, alkyl or arylsulfonates or alcohols are readily hydrolyzed to the original alcohols when treated with an aqueous base, and hence anhydrous solvolysis of the sulfonate (I) was first tried by the present inventors without success. After many strenuous efforts, the present inventors surprisingly have found that when the sulfonate (I) in 1,2-dimethoxyethane is treated with an aqueous sodium hydroxide, a new compound is detected on thin-layer chromatogram, and the compound is gradually converted into another new compound which shows λmax at 280 nm. The former is the deblocked sulfonate (II) and the latter is isocoformycin.

The base-treatment in Method-A is carried out either in a heterogenous system or in a homogenous one at a temperature of 0°-50° C.

In the heterogenous method, the sulfonate (I) is dissolved in a water-immiscible organic solvent such as methylene chloride, 1,2-dichloroethane, epichlorohydrine, 1,1,2,2-tetrachloroethane, chloroform, benzene, and toluene, and treated with an organic or inorganic base, preferably in the presence of a phase-transfer reagent such as tetra-n-alkylammonium halide wherein the alkyl has 3-12 carbon atoms or tetra-n-alkylphosphonium halide wherein the alkyl has 3-12 carbon atoms.

The preferable reaction conditions are as follows:

The sulfonate (I) is dissolved in methylene chloride and more than 10 equivalents of 0.5 N sodium hydroxide is added to the solution. Then about 0.05 equivalent of the phase-transfer reagent is added to the reaction mixture and the heterogenous reaction mixture is vigorously stirred at room temperature until no starting sulfonate (I) is detected on thin-layer chromatogram.

As the base, inorganic bases such as alkali metal or alkaline earth metal hydroxides, for example, sodium, potassium, calcium, barium, and magnesium hydroxide, or an alkali metal alcoholate, for example, sodium and potassium methoxide or ethoxide, or aluminum hydroxide, organic bases, for example, 1,8-diazabicyclo[5,4,0]-undecene-7, morpholine, cyclohexylamine, piperidine, thiomorpholine, and a basic ion-exchange resin are employed.

In the homogenous method, the base-treatment is carried out without the phase-transfer reagent in a water-miscible organic solvent such as acetone, dioxane, 1,2-dimethoxyethane, tetrahydrofuran, acetonitrile, dimethyl sulfoxide, or dimethylformamide. As the base, the above-mentioned ones are also employed.

In Method-B, the deblocking is carried out by treating at room temperature the sulfonate (I) with an alcoholic ammonia such as methanolic or ethanolic ammonia or with an anion-exchange resin when R in the sulfonate (I) represents the acyl, benzoyl, or the substituted benzoyl, or with a mild acidic reagnet such as acetic acid, trifluoroacetic acid, or an acidic ion-exchange resin when R in the sulfonate (I) represents isopropylidene, trityl, or the substituted trityl. The compound (II) is isolated and treated in an aqueous medium with the above-mentioned base. The base-treatment is conducted at a temperature of 0°-50° C., preferably at room temperature.

The sulfonate (I) is a known compound when R' is methyl (M. Ohno et al., J. Amer. Chem. Soc. 96, 4326 (1974).

The sulfonate (I) is prepared by causing 9-β-D-ribofuranosyl-6-hydroxymethyl-1,6-dihydropurine protected on hydroxyl groups in the ribose moiety of the formula:

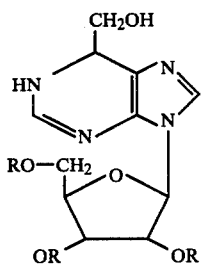

(IV)

wherein R represents the same as in the compound (I) to react with a reagent of the formula:

R'—SO$_2$X  (V)

wherein R' represents the same as in the compound (I) and X represents halo or imidazole, such as mesyl chloride, phenylsulfonyl halide, p-methyl- or p-halophenylsulfonyl halides, benzylsulfonyl halide, p-nitrobenzylsulfonyl halide, alkylsulfonyl imidazoles, alkoxyalkylsulfonyl imidazoles, p-alkyl- or p-halophenylsulfonyl imidazoles, benzylsulfonyl imidazole or p-nitrobenzylsulfonyl imidazole.

The reaction is carried out at room temperature in an inert organic solvent such as acetone, 1,2-dimethoxyethane, or dioxane, preferably in the presence of a weak base such as sodium or potassium carbonate and pyridine in an inert gas atmosphere.

The sulfonate (I) is also prepared by treating the compound (IV) with sodium hydride in dry tetrahydrofuran or 1,2-dimethoxyethane, followed by addition of the reagent (V).

The compound (IV) is prepared from 9-(2', 3', 5'-tri-O-acetyl-β-D-ribofuranosyl) purine by the method of Linschitz and Connolly, [H. Linschitz, J. S. Connolly, J. Am. Chem. Soc., 90, 2980(1968)] [M. Ohno, N. Yagisawa, S. Shibahara, S. Kondo, K. Maeda and H. Umezawa, J. Am. Chem. Soc., 96, 4326(1974)]. The deacetylated compound of (IV) is known to be an inhibitor of adenosine deaminase. [B. Evans, R. Walfenden, J. Am. Chem. Soc. 92, 4751(1970)].

Therefore, the overall processes for preparing isocoformycin can be shown by the following reaction formula:

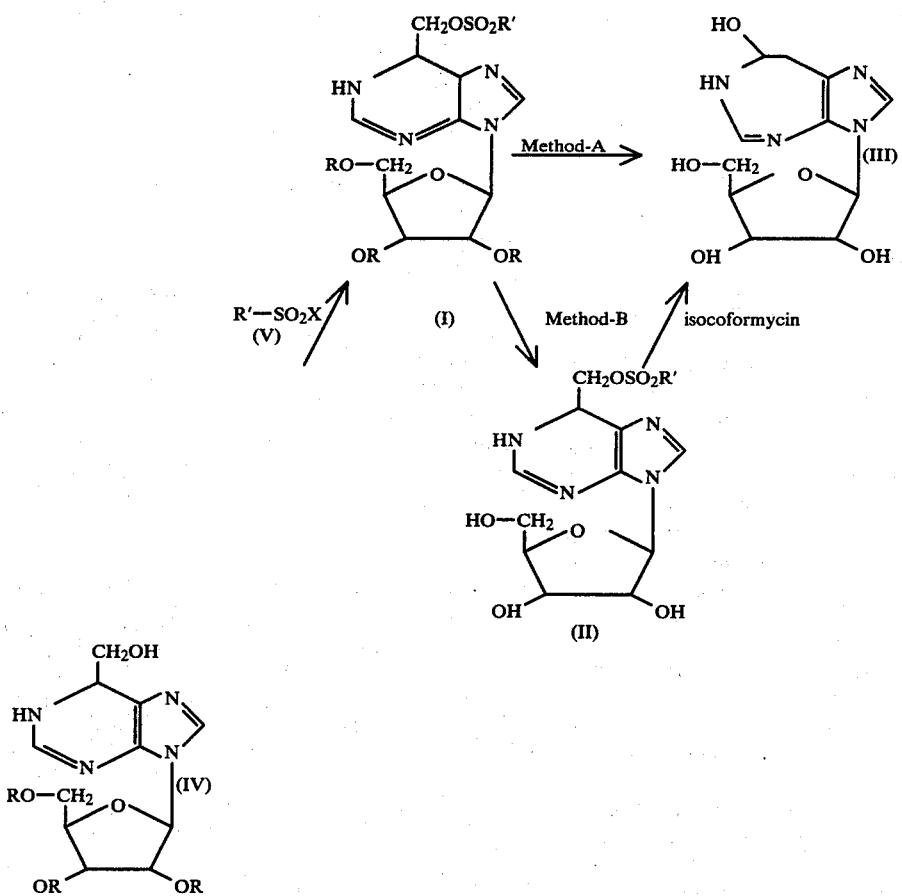

wherein R, R', and X represent the same as previously mentioned.

The isolation of the product, isocoformycin, is carried out, for example, as follows:

After the reaction of the compound (I) or (II) with a base, the aqueous alkaline solution freed from organic solvent is neutralized with acetic acid and diluted with water to about five volumes. The solution is charged to a column of a polystyrene nuclear sulfonic acid cation exchange resin (Dowex 50W and Amberlite IR120 are useful) and the chromatogram is developed with aqueous ammonia.

Evaporation of the eluate having λmax at 280 nm gives a yellow powder of crude isocoformycin. Further purification by silica gel or cellulose column chromatography affords pure isocoformycin. Isocoformycin is recrystallized from water or a combination of water and a suitable organic solvent, for example, methanol, ethanol or acetone. The following examples are included for the purpose of illustration.

DESCRIPTION OF THE PREFERRED EMBODIMENTS

EXAMPLE 1

6-Mesyloxymethyl-9-(2', 3', 5'-tri-O-acetyl-β-D-ribofuranosyl)-1,6-dihydropurine (I)

The alcohol (IV) which was prepared from 9-(2', 3', 5'-tri-O-acetyl-β-D-ribofuranosyl) purine by the method of Linschitz and Connoly [J. Am. Chem. Soc., 90, 2979 (1968)] was dissolved in dry acetone (60 ml) and anhydrous $K_2CO_3$ (4.5 g) was added. Mesyl chloride (0.57 ml, 840 mg) was then added all at once at room temperature under argon atmosphere and the mixture was vigorously stirred until no starting material was detected on TLC (ca. 2 hr).

The inorganic materials were removed by filtration and washed with fresh acetone. The combined filtrate and washings were evaporated under reduced pressure to leave a yellow foam of the mesylate (I, R=acetyl, R'=methyl):

yield 1.65 g (95%); UV $\lambda_{max}^{MeOH}$ 297 nm (ε 3900), 290 nm (ε 4300 at pH 1); $[\alpha]_D^{24}$ −17° (c 1.5, MeOH); MS: 393 (M+—OMs), 349(393-Ac), 333(393-OAc), 259(triacetylribose); IR(KBr): 3400, 1745, 1610, 1580, 1360, 1230, 1175, 1050 cm$^{-1}$; $^1$H-NMR (CDCl$_3$): δ 2.11(9H, s, Ac), 3.01(3H, s, SCH$_3$), 4.30–4.50(5H, m, 5'—CH$_2$, —CH$_2$OMs, H$_4$,), 5.34(1H, t, 6-CH), 5.50–6.00(3H, m, H$_{1'}$, H$_{2'}$, H$_{3'}$), 7.10(1H, s), 7.50(1H, s).

EXAMPLE 2

6-Tosyloxymethyl-9-(2', 3', 5'-tri-O-acetyl-β-D-ribofuranosyl)-1,6-dihydropurine (I)

The alcohol (IV, 215 mg) was dissolved in dry 1,2-dimethoxyethane (10 ml) and sodium hydride (76 mg) was added all at once at room temperature. The reaction mixture was stirred under argon atmosphere for 1 hr and tosyl imidazole (400 mg) was added, then stirred for 4 hr when TLC showed no starting material. Phosphate buffer (0.4 M, pH 6.5, 50 ml) was added and extracted with chloroform (25 ml×2), washed with 5% NaHCO$_3$ and water, and dried over Na$_2$SO$_4$. Removal of the solvent afforded the tosylate (I, R=acetyl, R'-p-methylphenyl) as a yellow foam (211 mg, 82%).

EXAMPLE 3
Isocoformycin (III)

The mesylate (I, 410 mg) obtained in Example 1 was dissolved in 1,2-dimethoxyethane (10 ml) and 1 N NaOH (10 ml) was added. The homogeneous brown solution was then stirred for 16 hr at room temperature, when no mesylate (I) was detected on TLC.

The organic solvent was removed under reduced pressure.

The residual aqueous solution was neutralized with acetic acid to pH 7, and diluted with water to 50 ml. It was then charged to a column of Dowex 50WX2 (NH$_4$+ form, 80 ml) and the chromatogram was developed with 0.5 N NH$_4$OH. The fractions having λmax at 280 nm were all combined and concentrated to yield a yellow powder (100 mg). Finally, a colorless powder of isocoformycin (51 mg, 21%) was obtained by silica gel chromatography with EtOAc-MeOH (5:1 in volume).

EXAMPLE 4
Isocoformycin (III)

The tosylate (I, 211 mg) obtained in Example 2 was dissolved in acetonitrile (10 ml) and 0.5 N Ba(OH)$_2$ (10 ml) was added. The homogeneous brown solution was then stirred for 4 hr, when no tosylate (I) was detected on thin-layer chromatogram. After treating the reaction mixture as in Example 2, isocoformycin (21 mg, 20%) was obtained.

EXAMPLE 5
Isocoformycin (III)

The mesylate (I, 68 mg) obtained in Example 1 was dissolved in 1,2-dichloroethane (4 ml) and 1 N NaOH (1 ml) was added. After addition of tetra-n-butylammonium bromide (6 mg) as a phase-transfer reagent the heterogeneous reaction mixture was vigorously stirred at room temperature for 3 hr. The unchanged mesylate was recovered from the organic layer (30 mg, 44%). Isocoformycin (14 mg, 35%; or 62% corrected) was isolated from the aqueous phase in the same manner as described in Example 3.

EXAMPLE 6
9-β-D-ribofuranosyl-6-mesyloxymethyl-1,6-dihydropurine (II)

The mesylate (I, 1.65 g) produced by the method described in Example 1 was treated with 20% methanolic ammonia (20 ml) for 1 hr at room temperature and evaporation of the solvent gave a brown foam (1.4 g).

Analytical sample was obtained by silica gel column chromatography with EtOAc-MeOH (5:1 in volume): UV λ$_{max}^{MeOH}$ 285 nm (ε 3760); [α]$_D^{25}$ −38° (c 1.0, MeOH); $^1$H-NMR(D$_2$O, 100 MHz): δ 3.55(3H, s, SCH$_3$), 4.26(2H, m, 5'-CH$_2$), 4.67(1H, m, 4'H), 4.75(1H, m, 3'H), 4.83(2H, m, -CH$_2$OMs), 5.10(1H, m, 2'H), 5.72(1H, t, 6-CH), 6.18(1H, d, 1'H), 7.64(1H, s, 2-H), 8.11(1H, s, 8-H).

EXAMPLE 7
Isocoformycin (III)

The mesylate (II, 1.4 g) obtained in Example 6 was treated with 1N NaOH (40 ml) for 1 hr at room temperature. The reaction mixture was neutralized with acetic acid to pH 7 and diluted with water to 200 ml.

It was then charged to a column of IR120 (NH$_4$+:H+=1:1, 100 ml) and the chromatogram was developed with 0.5 N NH$_4$OH to give a yellow powder (553 mg). The powder was further purified by silica gel column chromatography with EtOAc-MeOH-H$_2$O (5:1:1 in volume) to offer a colorless powder of isocoformycin (400 mg, 40%) from alcohol.

We claim
1. The compound, designated isocoformycin, having the formula

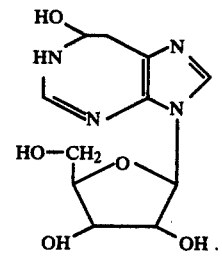

* * * * *